United States Patent US 8,538,816 B2
Campbell et al. Sep. 17, 2013

(54) METHOD OF REWARDING THE VIEWING OF ADVERTISEMENTS BASED ON EYE-GAZE PATTERNS

(75) Inventors: Christopher S. Campbell, San Jose, CA (US); Paul Philip Maglio, Catheys Valley, CA (US)

(73) Assignee: International Business Machines Corporation, Armonk, NY (US)

( * ) Notice: Subject to any disclaimer, the term of this patent is extended or adjusted under 35 U.S.C. 154(b) by 1621 days.

(21) Appl. No.: 10/906,021

(22) Filed: Jan. 31, 2005

(65) Prior Publication Data

US 2005/0108092 A1 May 19, 2005

Related U.S. Application Data

(62) Division of application No. 09/649,608, filed on Aug. 29, 2000, now Pat. No. 6,873,314.

(51) Int. Cl.
*G06Q 30/00* (2012.01)

(52) U.S. Cl.
USPC .......... 705/14.69; 705/14.68; 705/14.73; 345/156

(58) Field of Classification Search
USPC .......... 705/14.69, 14.68, 14.73; 345/156
See application file for complete search history.

(56) References Cited

U.S. PATENT DOCUMENTS

| | | | | |
|---|---|---|---|---|
| 5,794,210 A * | 8/1998 | Goldhaber et al. | ............ | 705/14 |
| 5,886,683 A * | 3/1999 | Tognazzini et al. | ........... | 715/700 |
| 6,106,119 A * | 8/2000 | Edwards | ....................... | 351/209 |
| 6,437,758 B1 * | 8/2002 | Nielsen et al. | .................... | 345/8 |
| 6,446,862 B1 * | 9/2002 | Mann | ............................ | 235/380 |
| 6,577,329 B1 * | 6/2003 | Flickner et al. | ............... | 715/774 |
| 2003/0033199 A1 * | 2/2003 | Coleman | ........................ | 705/14 |

OTHER PUBLICATIONS

Pieters, Rik et al. "Visual Attention to Repeated Print Advertising: A Test of Scanpath Theory". Journal of Marketing Research, Nov. 1999.*

* cited by examiner

*Primary Examiner* — Michael Bekerman
(74) *Attorney, Agent, or Firm* — IP Authority, LLC; Ramraj Soundararajan

(57) ABSTRACT

Users are rewarded for viewer interaction (based on tracked eye-gaze patterns) with Internet advertisements rendered on a display (such as a computer display), wherein the reward is computed based on the visual activity of the viewer. Payments are disbursed to any of the following: viewer, sponsor of the advertisement, creator of advertisement. Examples of reward computations include, but are not limited to, computing payments based on: the level of viewer interaction with the rendered advertisements, the amount/proportion of content interacted with by the viewer, the value of the text interacted with by the viewer. In one example, rewards are based on a combination of previously recorded viewer interests and computed payments based on user interaction.

20 Claims, 12 Drawing Sheets

METHOD OF REWARDING THE VIEWING OF ADVERTISEMENTS BASED ON EYE-GAZE PATTERNS

RELATED APPLICATIONS

This application is a divisional of U.S. application Ser. No. 09/649,608, filed Aug. 29, 2000.

BACKGROUND OF THE INVENTION

The present invention relates generally to the field of computer user interface technology. More specifically, the present invention is related to a system and method for the recognition of reading, skimming, and scanning from eye-gaze patterns.

The following definitions may assist in the understanding of the terminology used through the specification:

heterogeneous content—objects (like icons, windows, menus, etc.) encountered in electronic displays (e.g., monitors).

reading—a method of systematically and methodically examining and grasping the meaning of textual content.

skimming—a method of rapidly moving the eyes over textual content with the purpose of getting only the main ideas and a general overview of the content.

scanning—a method of rapidly covering a great breadth of the display in order to locate specific heterogeneous content.

tokenization—the process of classifying a range of phenomena (i.e. eye movements) into discrete categories.

quantization—integration (usually averaging) of a sequential group of measurements where the measurements in each group do not overlap. The measurements may be over time or space.

database—any stored collection of information located on the local computer, a local area network (LAN) or and wide area network (WAN) including the world wide web (WWW). (note: any use of this term refers to the use of the term as defined in this way.)

DISCUSSION OF PRIOR ART

Computers are a widely used resource in today's society. In most systems a user manipulates a keyboard or a mouse to communicate with a computer. Modern systems include a graphical user interface (GUI) which communicates with the user by displaying various heterogenous content. In the context of this patent application, heterogeneous content includes objects normally encountered on computer monitors. For example, as illustrated in FIG. 1, heterogeneous content 100 includes (but is not restricted to) any of, or a combination of: text 102, images 104, hyperlinks 106, windows 108, icons 110, or menus 112. When users view a computer monitor with heterogeneous content displayed on its screen, they utilize an input device, such as a mouse or a keyboard, to manipulate one (or a combination of) heterogenous content items based on their interests. FIG. 2 illustrates a prior art system which comprises monitor 200, computer CPU unit 202, mouse 204, and keyboard 206. Users view on the computer monitor 200 various heterogeneous content items (like A, B, and C) and, based on their interest, they interact with one or more or a combination of heterogeneous content items via mouse 204 or keyboard 206. This step is very "user driven" since the system does not have a means for dynamically tracking user interests (whether they are interested in A, B, or C) regarding the displayed heterogenous content and hence the computer waits for the user to respond via an input device before proceeding with any action.

Thus, there is a need for a system that can dynamically and accurately determine what heterogenous content a user is interested in and the relative level of interest. One way of determining this relative interest level is by detecting what area of the display the user holds eye movement to a minimum (e.g., maintains a gaze). Yet another related way involves determining user interests by detecting (from eye-movement patterns or eye-gaze patterns) which part of the heterogenous display screen was read by the user.

Detecting when a user is reading rather than merely scanning or skimming from eye-gaze patterns is a difficult problem, as low-level eye movements are almost completely automatic (i.e., involuntary). Thus, low-level eye movements do not follow the assumed pattern of right→right→right during reading but instead follow much more complex patterns.

FIG. 3 illustrates some of the common eye movements observed during reading. Common eye movement behaviors observed in reading 300 include forward saccades (or jumps) 302 of various length (eye-movements to the right), micro-saccades (small movements in various directions) 304, fixations of various duration 306, regressions (eye-movements to the left) 308, jitters (shaky movements) 310, and nystagmus (a rapid, involuntary, oscillatory motion of the eyeball) 312. As illustrated by FIG. 4, these behaviors in turn depend on several factors 400, some of which include (but are not restricted to): text difficulty 402, word length 404, word frequency 406, font size 408, font color 410, distortion 412, user distance to display 414, and individual differences 416. Individual differences that affect eye-movements further include, but are not limited to, reading speed 418, intelligence 420, age 422, and language skills 424. For example, as the text becomes more difficult to comprehend, fixation duration increases (as described by Just & Carpenter in their paper entitled, *A theory of reading: From eye fixations to comprehension*, Psychological Review, 1980) and the number of regressions increases (as described by Rayner & Frazier in their paper entitled, *Parsing temporarily ambiguous complements*, Quarterly Journal of Experimental Psychology, 1987.) Given the complexity of eye-gaze patterns and the detailed information about the text and the individual required to predict these patterns, there have been no attempts to build a system to recognize reading until now.

Recent work in intelligent user interfaces has focused on making computers similar to an assistant or butler in supposing that the computer should be attentive to what the user is doing and should keep track of user interests and needs. Because the Microsoft Windows® operating system and other windows-based operating systems are ubiquitous and visually intensive, researchers have identified eye-gaze as a valuable way to determine user interest when interacting with most computer terminals. An effort to capitalize on eye-gaze as a measure of user interest was made in U.S. Pat. No. 5,886,683, which describes a method and apparatus for providing relevant information based on eye-gaze. In this case, interest in some display object (icon, image, or block of text) was determined based on a fixation threshold. Simply put, if the user looks at an object on the screen long enough, the system infers that the user is interested in that object. This same rule also applies to blocks of text. But, there is a need to determine different levels of user interest based on the type of user behavior, such as reading (high interest), skimming (medium), or scanning (low interest) as well as capturing the exact words on the screen that are involved.

Other researchers have been concerned more specifically with making sense out of complex, low level eye movement data. As noted, the eye is constantly moving. Even when one seems to be looking steadily at some object, the eye still makes micro-saccades (small movements), jitters (shaky movements), and nystagmus (compensatory movements to head motion). To provide eye movement data that is closer to what users experience, researchers have attempted to break down or filter complex raw eye movement data into a set of tokens. Work on fixation recognition that has formed the core of this research area was originally proposed by Jacobs in his paper entitled, *Eye movement-based human-computer interaction techniques: Toward non-command interfaces*, Advances in Human-Computer Interaction, 1990; and later in his paper entitled, *What you look at is what you get: Eye movement-based interaction techniques*, Proceedings ACM CHI '90 Human Factors in Computer Systems, 1990. The term "fixation" refers to an area of relatively stable gaze that lasts between 30 and 800 milliseconds. Although people are not aware of micro-saccades, they do report areas of fixation. Thus, fixation recognition is an attempt to determine where a user intended to look. Jacob's fixation recognition algorithm works by taking a 100 millisecond set of data (6 data points for this implementation) and if the points are all within 0.5 degrees of visual angle, then a fixation is said to be detected and located at the average point. The fixation continues as long as the gaze points stay within 1.0 degree of this average fixation point.

Obviously, the goal of Jacob's method is far different from that of the present invention's goal of recognizing reading. Let us assume that his method for fixation recognition is used by a simple algorithm for reading detection. For instance, suppose a series of say three fixations to the right, fixation→fixation→fixation, signal that reading is detected. Several problems occur when using this method for reading detection: (a) loss of information, (b) regressions, (c) eye movement on the Y axis, (d) resets to beginning of next line, (e) revisits to previous sentences.

Whatever the precise merits, features, and advantages of the above cited references, none of them achieves or fulfills the purposes of the present invention.

SUMMARY OF THE INVENTION

The present invention is an implemented method for rewarding users for viewing Internet advertisements rendered on a display, wherein the method comprises: (a) determining viewer interaction with content of rendered advertisements based on eye-gaze patterns; (b) recording viewer interests based on determination in (a); (c) computing payments based on viewer activity; and (d) disbursing payments based on computed payments. Payments are disbursed to any of, but are not limited to, the following: viewer, sponsor of the advertisement, creator of advertisement.

Examples of reward computations include, but are not limited to, computing payments based on: the level of viewer interaction with the rendered advertisements, the amount/proportion of content interacted with by the viewer, the value of the text interacted with by the viewer.

In one embodiment, the level of viewer interaction comprises determining if said viewer is reading, skimming, or scanning said rendered content of said advertisement.

In one embodiment, recorded viewer interests are stored in a remote database and, in addition to said viewer activity, reward payments are computed based on previously recorded viewer interests.

DESCRIPTION OF THE PREFERRED EMBODIMENTS

Figure 1:
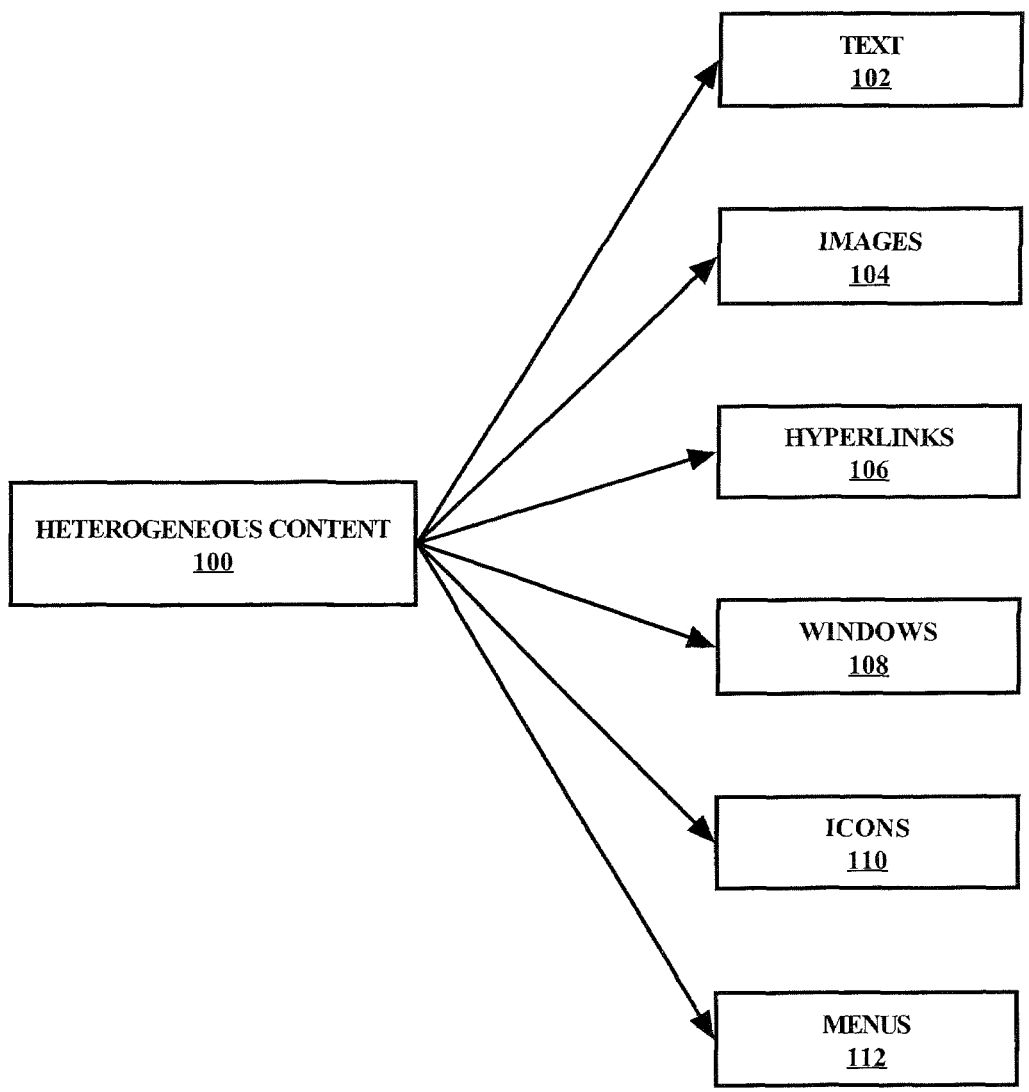
FIG. 1 illustrates examples of various heterogeneous content.
Figure 2:
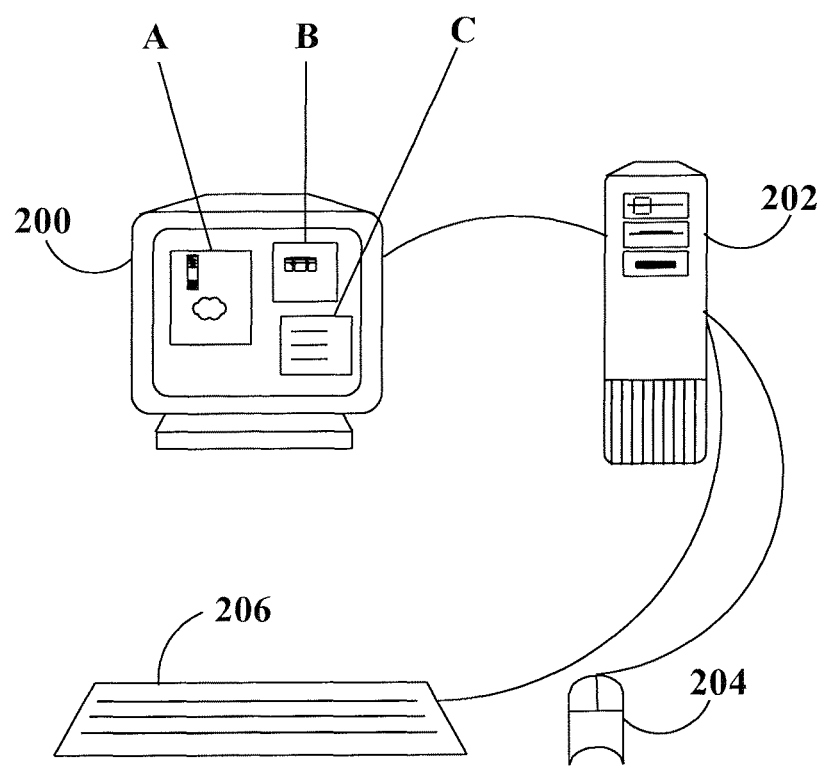
FIG. 2 illustrates prior art system showing a general computer setup.
Figure 3:
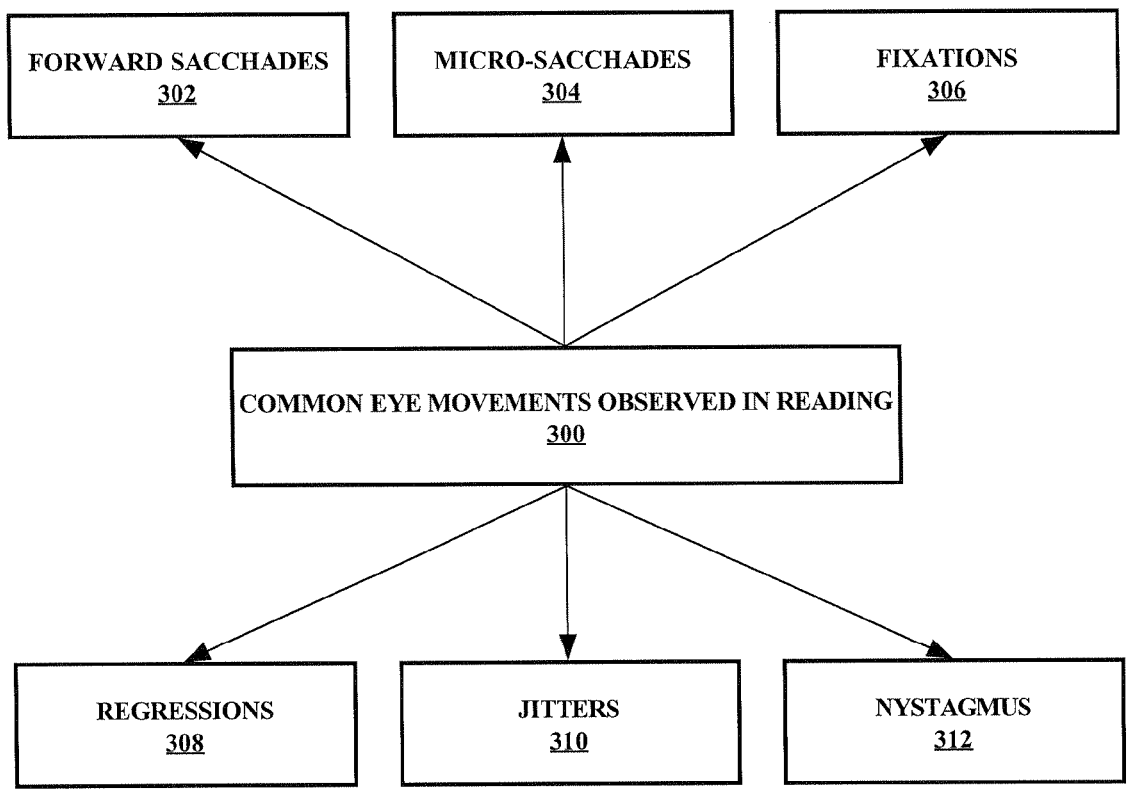
FIG. 3 illustrates common eye movements observed in reading.
Figure 4:
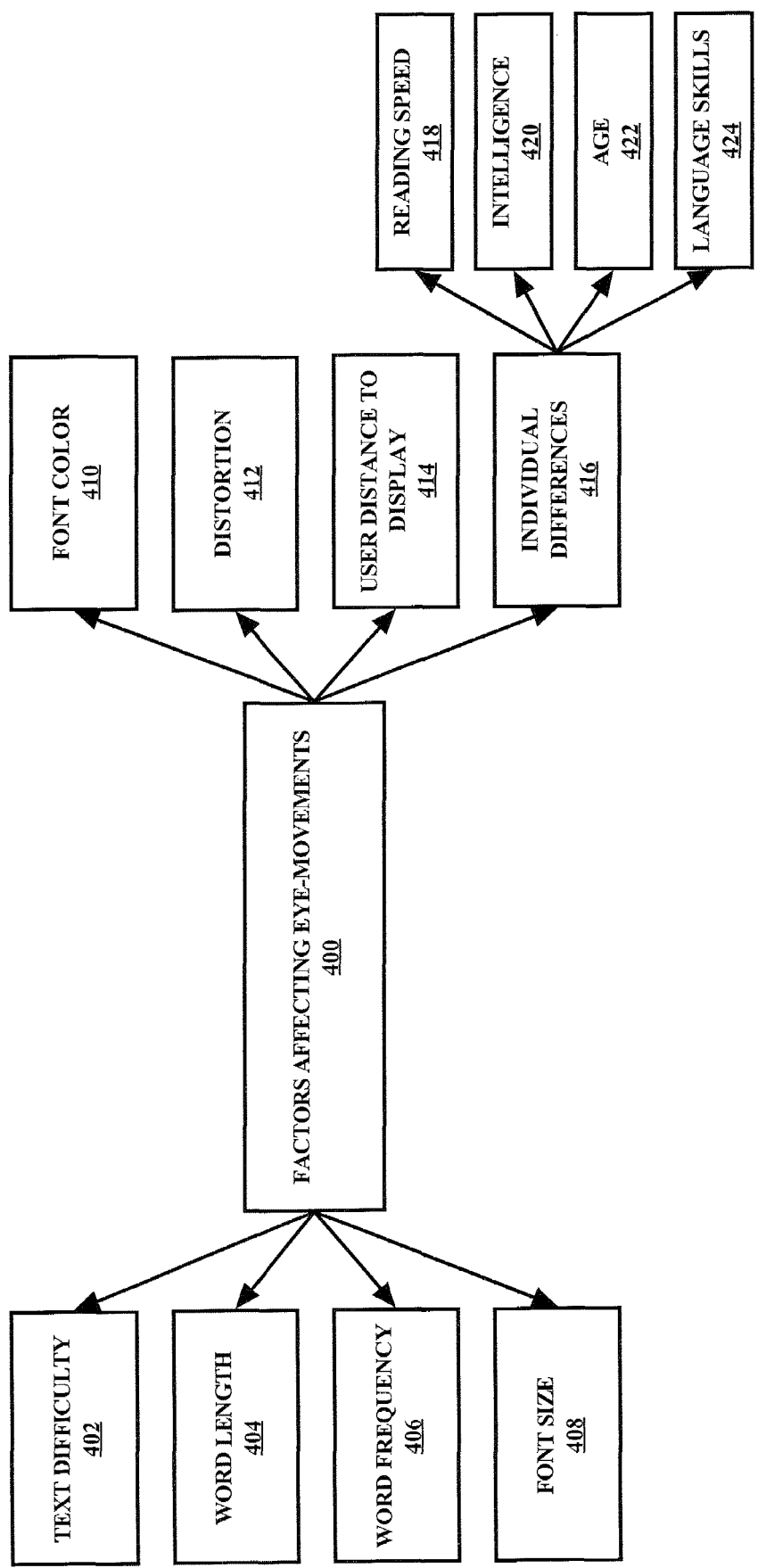
FIG. 4 illustrates some of the factors affecting eye movements.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Figure 5:
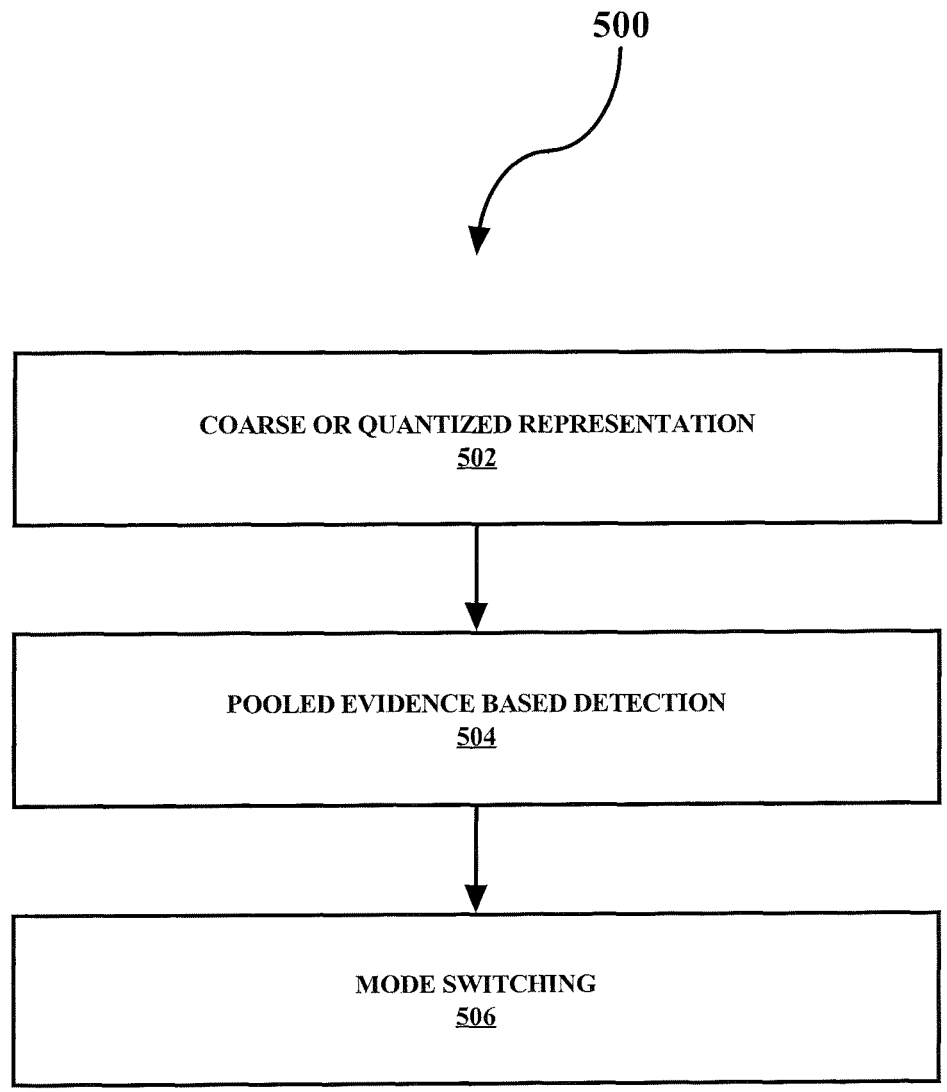
FIG. 5 illustrates a method for recognizing, from eye-gaze patterns, when a user is reading, skimming, or scanning on a display filled with heterogenous content.
Figure 6:
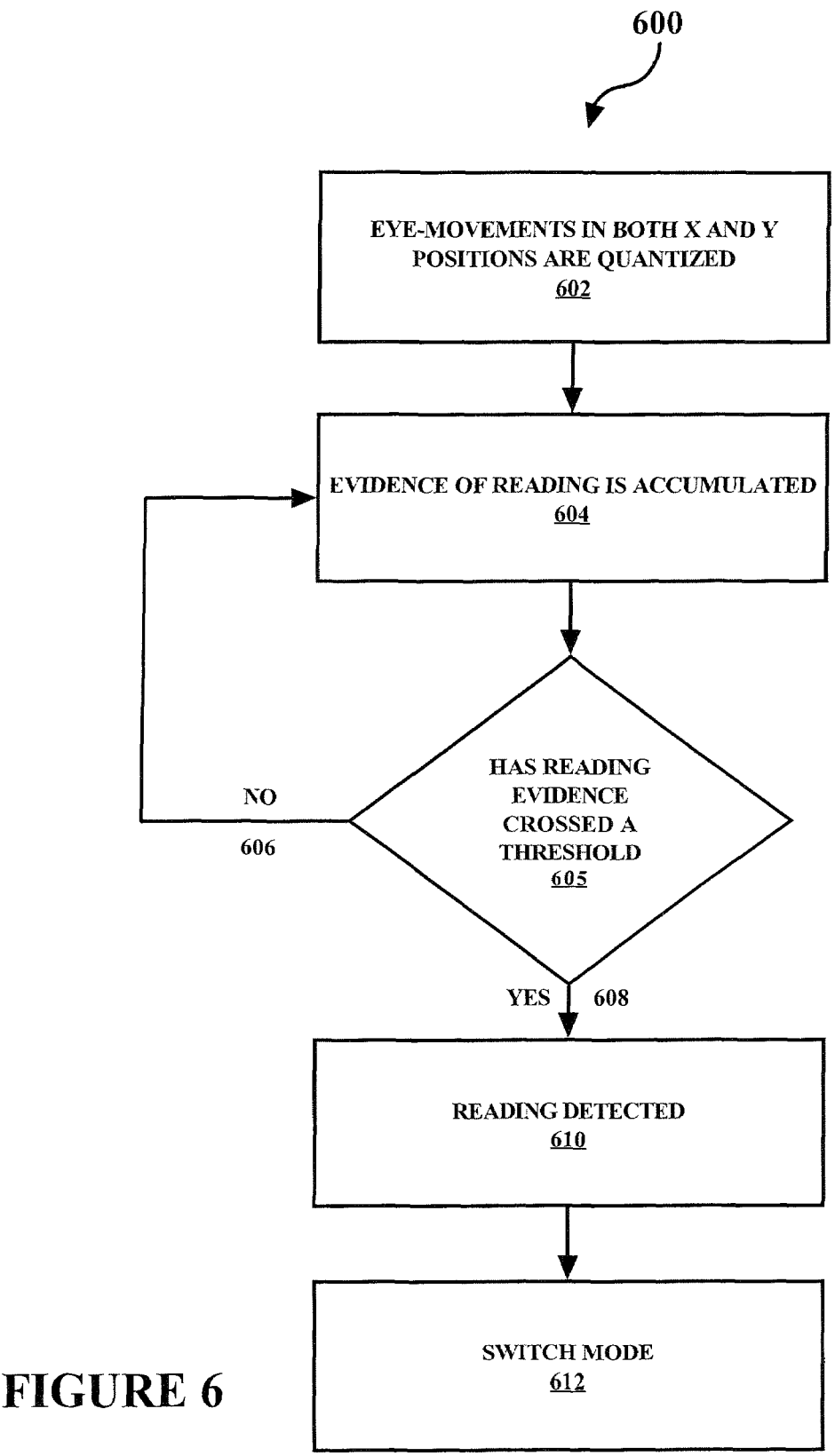
FIG. 6 illustrates the flowchart describing the functionality of the method in FIG. 5.

FIG. 5 illustrates a method 500 for recognizing, from eye-gaze patterns, when a user is reading, skimming, or scanning on a display filled with heterogeneous content. The method comprises three mechanisms: (1) coarse or quantized representation of eye-movements 502, (2) pooled evidence based detection 504, and (3) mode switching 506. This is further elucidated, as in FIG. 6, via a flowchart 600 describing the functionality of the above described method. First, the eye-movements in both x and y positions are quantized (and averaged) 602 over 100 ms intervals. This process removes some of the inaccuracy of prior art eye-tracking hardware and reduces the influence of micro-saccades. Second, evidence of reading is accumulated 604 until it crosses a threshold value 605. The system may increment a reading-evidence variable by 1, for instance, when the eye moves to the right and de-incrementing by 1, for instance, when the eye moves to the left. If the evidence reaches a threshold 608 of, say, 3, then "reading" is detected 610 and the mode switched 612 from scanning to reading. If the threshold is not reached 606, then the system continues to collect evidence of reading.

Pooled evidence acts to reduce the influence of eye movements back to previously read words (regressions or revisits)

and movements above and below the current line of text. Mode switching allows the present invention to essentially interpret the same eye movements differently, based on changes in context. For example, large eye movements to the left and slightly up mean, within a scanning context, that the user is continuing to scan, but within a reading context this movement is more likely to mean that the user is re-reading text and will continue the reading process. Depending on the difficulty of the text, users may often revisit text they have already read several sentences back to clarify ambiguities in the sentence they are currently reading. If this movement were only allowed to have one meaning, say that the user is scanning, then the tracking of reading would end prematurely on every revisit. If this movement were to only mean that the user is reading, then this would increase the number of false alarms or times the system detected reading when the user was not reading. Mode switching allows the present invention to account for this behavior in different contexts and as a result produce more robust reading detection and continuous, reliable read tracking.

Figure 7:
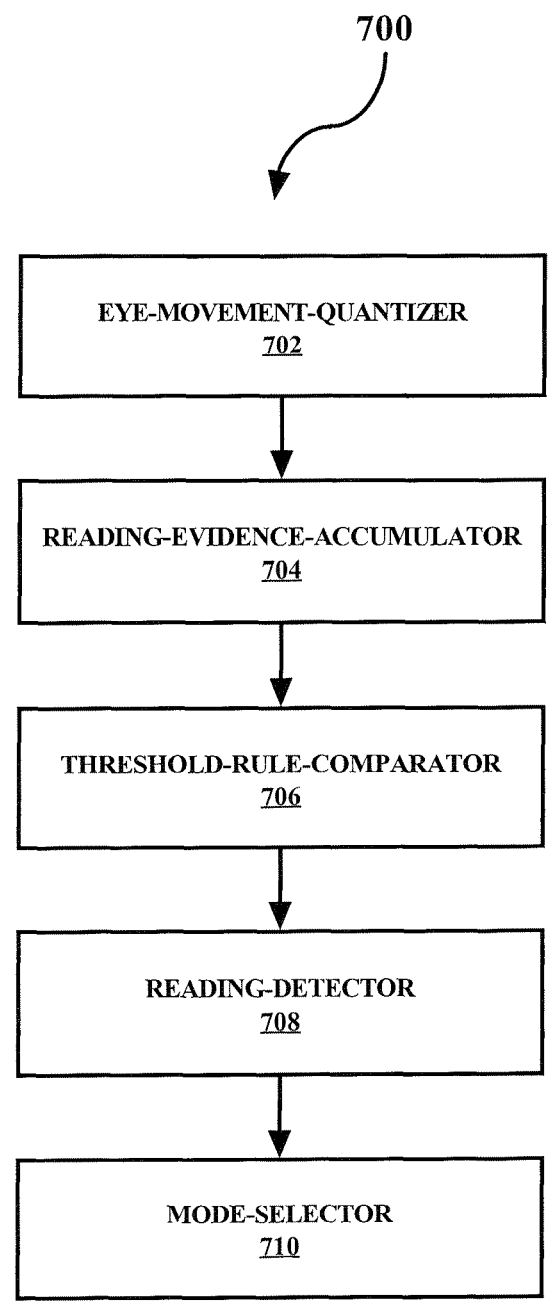
FIG. 7 illustrates a system for recognizing, from eye-gaze patterns, when a user is reading, skimming, or scanning on a display filled with heterogenous content.

FIG. 7 illustrates a system 700 for recognizing, from eye-gaze patterns, when a user is reading, skimming, or scanning on a display filled with heterogeneous content. The system comprises: eye-movement-quantizer 702 which quantizes the eye-movement in both the x and y directions, reading-evidence-accumulator 704 which accumulates evidence of reading, and a threshold-rule-comparator 706 which compares the reading evidence against a threshold. If the reading evidence is above the threshold, reading-detector 708 detects reading and mode switcher 710 switches the mode from scanning to reading.

Figure 8:
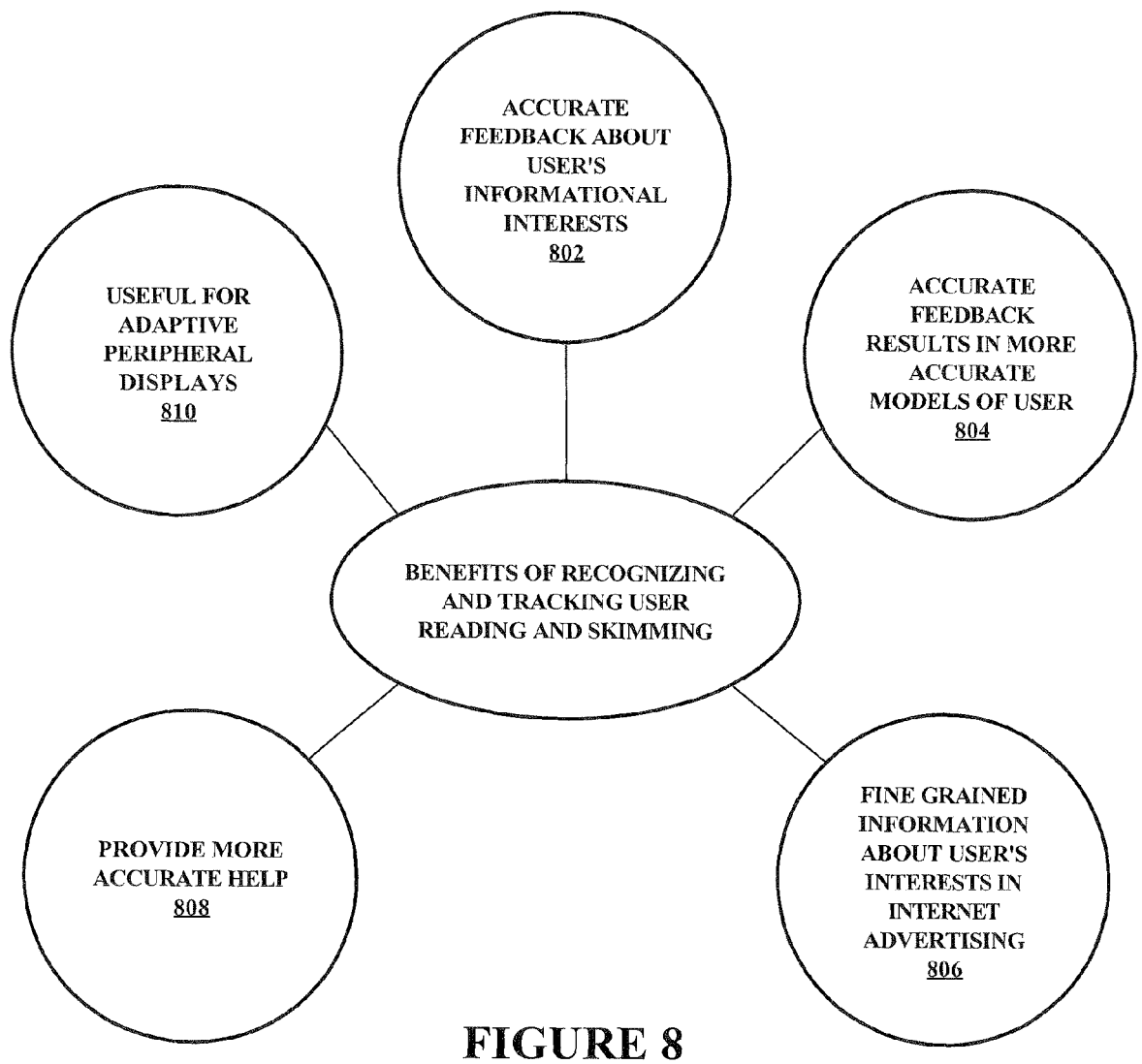
FIG. 8 illustrates the benefits of recognizing and tracking user reading and skimming.

FIG. 8 illustrates the benefits of recognizing and tracking user reading and skimming 800. Some of these benefits are discussed below:

A. One advantage is accurate feedback about the user's informational interests and needs 802. It is possible, for example, to infer that a user read the text of a web page just because a program detected the page being loaded in the browser and that the page remained in the browser for, say, 10 minutes. But, the user might have loaded the web page and then, seeing it is of no interest, switched to another application. The present invention provides a direct, fine-grained, and application-independent method to determine what text the user has read and therefore providing a better basis on which to infer what concepts are of interest to the user.

B. Another benefit is that more accurate feedback results in more accurate models of the user 804. Thus, the present invention provides relevant and personal assistance for a variety of tasks commonly performed with PC's, such as searching for information on the Web, writing manuscripts, composing e-mail, or looking for a certain type of news (e.g., articles about baseball). For example, if a user model shows that user always reads articles on Astronomy, the system could direct news gathering agents to get articles that a user might be interested in, and to organize (prioritize) information that has already been gathered.

C. A more specific benefit is fine-grained information about a user's interest in Internet advertising 806. Instead of merely measuring the amount of time the user looked at the advertisement (gaze-duration), the system records the text that the user read. Additionally, the present invention determines if the user carefully read the text or just skimmed it. Thus, in addition to mere banner click points, the system, as a business method, awards a user different levels of gaze points or different cash amounts based on this fine-grained information (e.g. non-reading gaze=10 cents, skimming gaze=20 cents, and reading gaze=40 cents). Payment rates are determined by level of user interaction with advertisements.

D. Another specific advantage is that by using gaze movements data, computer help systems are given more context information and therefore provide more accurate help 808. Current context-sensitive help systems such as WinHelp from Microsoft Windows® require the user to press the "?" button and then select the problem topic. By analyzing reading data, however, the present invention may determine, for example, which text was re-read, perhaps suggesting confusion, and may determine which words were fixated on, perhaps because of a lack of familiarity. The system uses this data to decide what help topics to suggest and in what order. Additionally, the help text could be customized to avoid terms that the user is not familiar with.

E. Finally, knowledge of whether the user is reading, skimming, or scanning is useful for creating adaptive peripheral displays 810. When the user is reading, the display should be as "quiet" or as non-distracting as possible by reducing motion and eliminating auditory feedback. However, when the user is scanning, the display can be more assertive with its suggestions; for instance, becoming larger, flashing new information in red, or by giving audio effects for stock market action (e.g., a cheering and clapping sound when a stock hits a new high).

Figure 9:
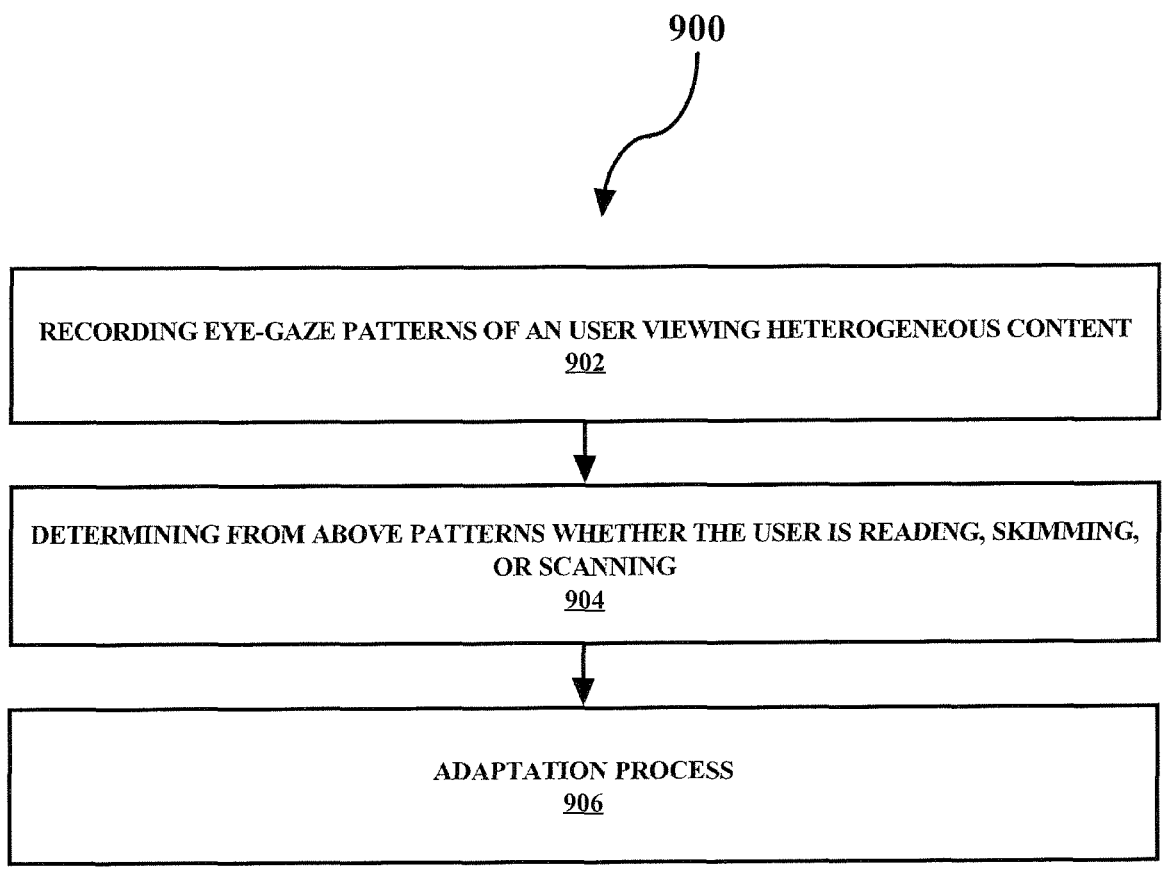
FIG. 9 illustrates a method for utilizing user interest information to adapt to a user's needs.
Figure 10:
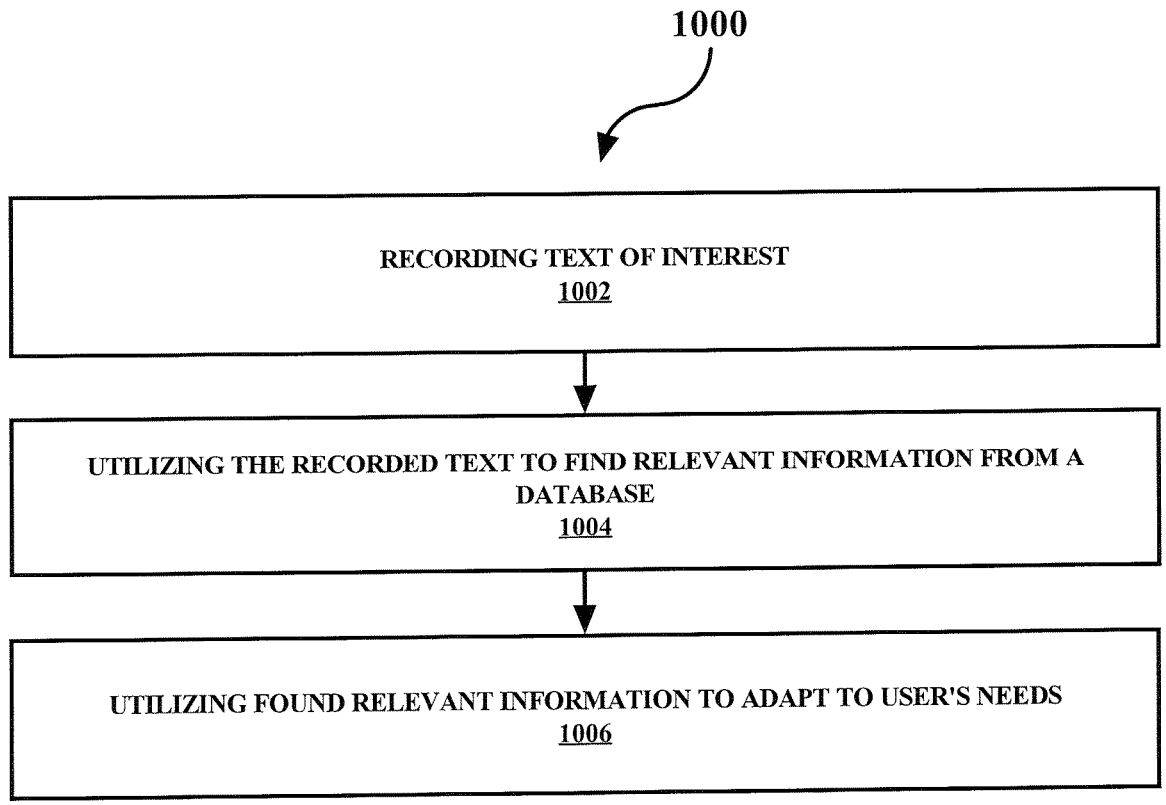
FIG. 10 illustrates the adaptation process of the method in FIG. 9.
Figure 11:
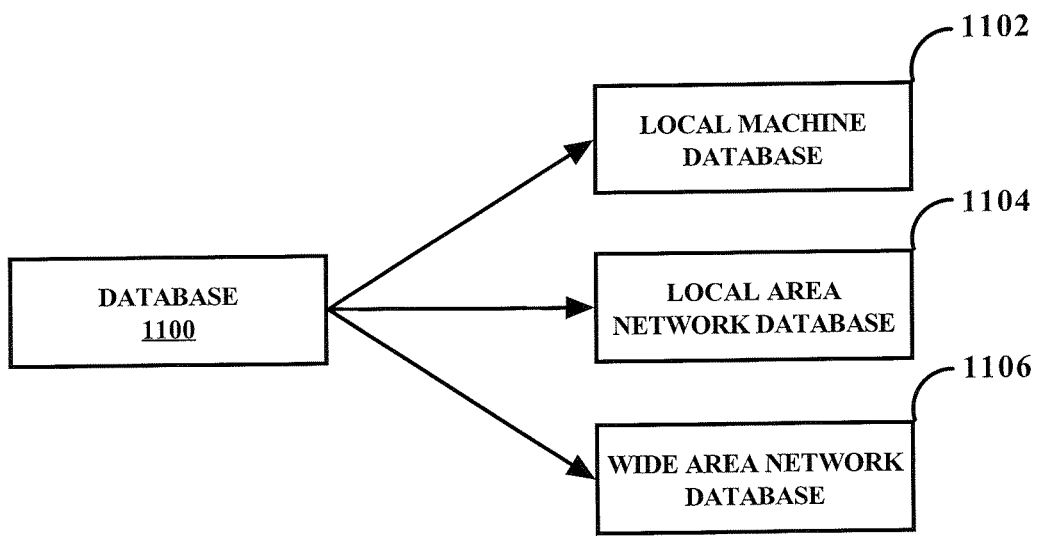
FIG. 11 illustrates the various databases that can be used in conjunction with the adaptation process described in FIG. 10.

In one embodiment of the invention, as illustrated in FIG. 9, the method 900 involves, first, recording the eye-gaze patterns of an user viewing heterogeneous content 902. Second, determining (as described above) from the patterns whether the user is reading, skimming or scanning 904. Last, the system uses information about what text the user is reading or skimming to infer user interest and uses this interest information to adapt to the user's needs via an adaptation process 906. FIG. 10 further illustrates the adaptation process 1000. First, the text that the user is interested in is recorded 1002. Next, the system utilizes the recorded text to find relevant information from a database 1004. Lastly, the retrieved relevant information is utilized to allow the system to adapt to the user's needs 1006. FIG. 11 further illustrates that the database 1100 of step 1004 is one of the following: local machine database 1102, local area network (LAN) database 1104, wide area network (WAN) database 1106 such as the World Wide Web.

Figure 12:
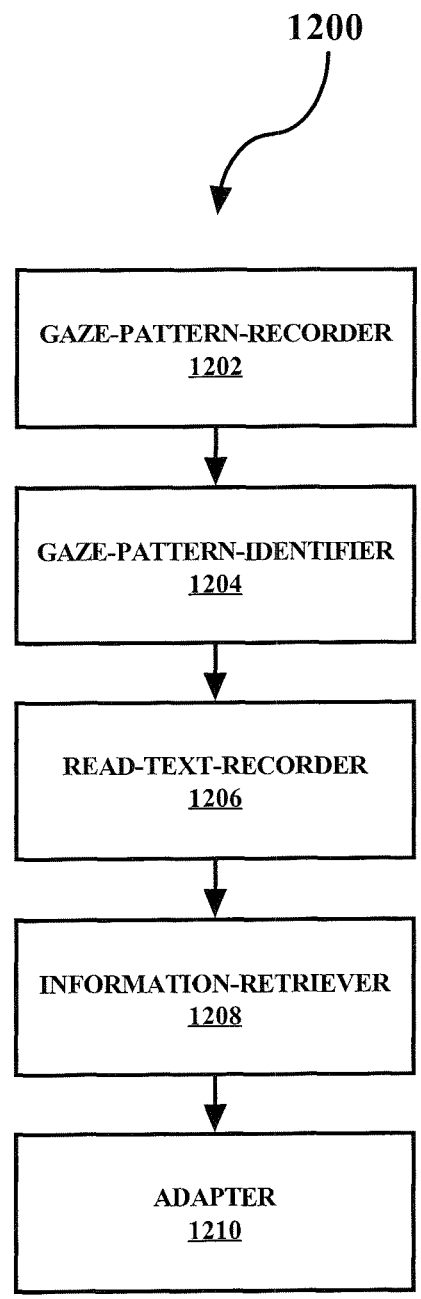
FIG. 12 illustrates the system for utilizing user interest information to adapt to a user's needs.

FIG. 12 illustrates a system 1200 to implement the above mentioned method. It comprises a gaze-pattern-recorder 1202 which records the gaze-pattern of a user, and a gaze-pattern-identifier 1204 which identifies whether a user is reading, skimming, or scanning. The system further includes a read-text-recorder 1206 which records the text that was read by the user. Lastly, the system includes an adapter 1210, to adapt to user needs. In one embodiment, an information-retriever 1208 retrieves relevant information (related to read text) from a database and the system utilizes this information to adapt to user needs.

Figure 13:
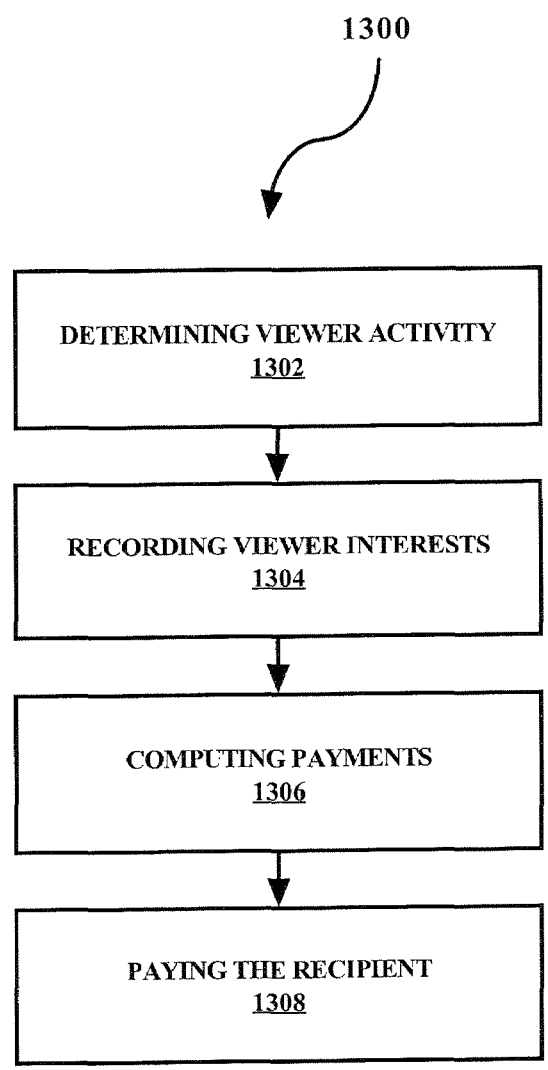
FIG. 13 illustrates a method of paying for Internet advertisements.

In another embodiment, as described by FIG. 13, the present invention is used in a method 1300 of paying for Internet advertisements. First, the method determines the user activity 1302 by determining whether a user is reading, skimming, or scanning. Next, the method records the user's interests 1304, for example, the system records text or words that the user is interested in. Furthermore, the method computes payments 1306 based on user activity and viewer interests and lastly, a payment is scheduled to the user 1308.

As stated above, payments for ad interaction could be computed based on the:

a) level of viewer interaction with the ad, (i.e. read, skimmed, or scanned), b) amount or proportion of text/content that the viewer interacts with (more content equals more payment), and
c) the value of the text that the viewer interacts with.

Here, text value could be based on general guidelines like the company name and slogan are more important than other text. Alternatively text value could be defined by the advertiser so that, for example, words that convey key concepts are more important than the company name. Payments could also be calculated based on the three factors given above combined with viewer demographics and databases with additional historical information about viewer's behavior and attitudes. Viewer demographics such as age, gender, race, SES, education, religion, etc., can be obtained voluntarily from the viewer or by viewer identification combined with advertiser or third party databases.

Ad interaction or interest could also be a basis for determining ad effectiveness. Ad effectiveness is how well the advertisement conveys the message that the creators intended and whether or not the advertisement ultimately contributes to revenue. By knowing which text in the ad the viewer read or skimmed, the amount of text read, and the values of the text read, the effectiveness of the ad can be determined. For example, if 60% of people who looked at the ad read the words that convey the central concept of the ad, one may conclude that the ad is fairly effective. However, if 90% of people who looked at the ad did not read far enough down the text to get to the main point, then one may conclude that the ad is ineffective. This could be due to the fact that there is too much text or that the topmost text does not capture and hold the viewer's attention. Demographics information from advertiser or third party databases could also be used to determine if the ads are reaching the target audience.

Payments for ad interaction can be made to the viewer of the ad and/or to the advertiser and/or even to the creator of the ad. As pointed out above, some business models are based on paying or providing a service for viewers that have advertisements on their display. By providing payments or compensation based on ad interest, advertisers could ensure that viewers are actually receiving the message that the advertisers are trying to convey. Also by paying or compensating advertisers based on ad interest, advertisers can get credit for effectively placing ads so that the ad gets attention. On Web sites, advertisers can get credit for ads that attract attention but may not necessarily lead to click-throughs. Such may be the case if the Web user is searching for information and does not have time to go to the advertiser's site but quickly reads the ad for future reference. The ad agency can also be paid or otherwise compensated for how much interest the ad generates as an incentive or as part of a compensation package. Compensation for ad interest or interaction for any of the above parties is not limited to monetary transactions but could include goods, services (free Internet Service Provider; see NetZero.com), reward points (see MyPoints.com), promotional items, contest entries, gift certificates, bonds, stock, stock options.

The above mentioned user interest information and ad effectiveness could be transmitted to and stored in the advertiser's database so that statistics on ad viewing could be compiled and processed. Additional statistics could be calculated and published indicating which ad hosts do the best job of displaying ads and which ad agencies create ads that get attention or are effective.

An implementation of the present invention that was made fully functional on Jul. 18, 1999, is now described in more detail as the preferred embodiment. The system tracks the text a user is reading on a computer screen (in any application or window) and sends that text to interest tracking software called Suitor (as described by Maglio et al. in their paper entitled, *SUITOR: An Attentive Information System*, The International Conference on Intelligent User Interfaces, 1999), which then acts on this text by (a) obtaining web pages that are related to keywords in the text and (b) adding the text to a user model. The method used by this system to detect reading rather than scanning includes three processes, (a) quantizing the eye movement data, (b) pooling eye movement evidence and applying a threshold, and (c) mode switching. The term scanning is used here to include both exploratory and searching eye movements. Exploratory eye movements are meant to inspect the objects on the screen whereas searching eye movements are meant to find a specific object or class of objects on the screen.

A preferred embodiment of the present invention includes a system which first quantizes raw data sent from the eye tracking hardware by averaging every 3 data points. This raw data is provided by the eye tracker at a rate of 30 points (X and Y positions) per second, but after averaging is reduced to 10 data points per second or one data point every 100 milliseconds. The system is initially in scanning mode, which requires a set of events to occur to switch into reading mode. The events that are tracked include the specific eye movements shown in Table 1. For example, if the eye moves a short distance left then the event is a "regression saccade" but if the eye moves a long distance left then the event is a "scan jump".

The quantized, tokenized stream of eye-movement data is then pooled to determine whether the user is reading. The pooled evidence for reading is calculated by taking the accumulated value of the pooled data and adding the points associated with the current event for both the X and Y axes. Thus, if a "read forward" event occurs for the X axis and a "skim jump" occurs for the Y axis then (10+−5)=5 points would be added to the pool. Note that it is possible to have no event occur for the X and/or Y axis if the eye does not move. Every non-event is given 0 points. For this implementation, the pooled evidence that a user is reading must cross a threshold of 30 points to switch into reading mode.

By using pooled evidence, the system does not have to look for a specific pattern of events but allows for a wide range of patterns to signal reading. Thus, reading recognition is tolerant to noise, maintains a high hit rate and low false alarm rate. For example, the events "read forward", "skim forward", "skim jump", "read forward", and "read forward" (10+5+−5+10+10=30 points) are sufficient to trigger reading detection. However, these five events may be ordered in different ways—there are exactly 20 possible permutations. Rather than looking for each of these 20 possible sets of events, pooled evidence allows the system to accumulate mounting evidence despite noise. Thus, increasing noise only delays reading detection but does not block it altogether. Ideally, the quickest reading could be detected is if the highly unlikely pattern, read forward→read forward→read forward, occurs. Because the system samples in 100 millisecond increments, 3×100=300 milliseconds or about one-third of a second is the fastest possible reading detection time.

Once the threshold is passed, reading is detected and mode changes from "scanning" to "reading" mode. In reading mode, the rules for changing back to scanning mode are different. The system records every word read in reading mode until a "scan jump" event is detected. A single "scan jump" event will send the system back into scanning mode. This method of mode switching allows for fairly quick changes in modes while still maintaining reliable read tracking. Reliable read tracking is important because readers will often show a wide range of behaviors while reading, including long pauses on ambiguous words, large regressions to text that may help to disambiguate the current sentence, and moderate forward jumps in anticipation of up-coming text.

Alternative embodiments include:

A. Skimming detection. The method for detecting skimming includes recording, in reading mode only, the distance of each eye-movement. If the distance is less than some threshold, then the words that the eye moved across are classified as read; but if the distance is greater than some threshold, then the words are classified as skimmed. In other words, if the eye moves quickly over some words then those words were skimmed.

B. Adaptive parameters. The method will include parameters that adapt to individual reading speeds and abilities by adjusting parameters that are used to determine the actual vales of the distances: short, medium, and long in Table 1. If, for example, the system determines that the user is a slow and careful reader, then all the distances (for the X axis) should be decreased to optimize performance. If, on the other hand, the system determines that the user's reading ability is poor, then more regressions will occur and the mode switching threshold should be decreased (to be more sensitive).

| Distance, direction, axis | Token | Points (Evidence for Reading) |
|---|---|---|
| short right X: | read forward | 10 |
| medium right X: | skim forward | 5 |
| long right X: | scan jump | resets the evidence counter |
| short left (back) X: | regression saccade | −10 |
| medium left X: | skim jump | −5 |
| long left X: | scan jump | resets the evidence counter |
| short up Y | skim jump | −5 |
| medium up Y | scan jump | resets the evidence counter |
| long up Y | scan jump | resets the evidence counter |
| short down Y | anticipatory saccade | 0 |
| medium down Y | skim jump | −5 |
| long down | scan jump | resets the evidence counter |
| long, medium left X and short, down Y | reset jump | 5 |

Note: Positive point values indicate evidence supporting reading and negative numbers indicate evidence against reading.

Table 1. Tokenization of Eye Movements and Evidence for Reading

C. Context information. The method will also include context information to constrain reading detection and improve accuracy and reliability. Useful context includes, (a) the location of text on the screen, (b) the size of the font, (c) the content of the text on the screen, (d) whether the user is scrolling, navigating, or pointing, and (e) the distance of the user from the screen. Mode switching between reading and scanning is improved by determining the size of the text on the retina of the eye, because this determines the size of eye movements in reading. In other words, the larger the text, the bigger the eye movements in reading. Determining the size of text on the retina requires knowing the size of the font and the distance of the user from the screen. For example, fine text is usually read more slowly. Finally, detecting the use of an input device may help to determine whether they are reading. For example, it is unlikely that the user is reading when navigating, pointing or scrolling (considering the jumpy scrolling behavior of a typical mouse).

The above enhancements for reading recognition systems and described functional elements may be implemented in various computing environments. For example, the present invention is implemented on a conventional IBM PC or equivalent, multi-nodal system (e.g. LAN) or networking system (e.g. Internet, WWW). All programming and data related thereto are stored in computer memory, static or dynamic, and may be retrieved by the user in any of: conventional computer storage, display (i.e., CRT) and/or hardcopy (i.e., printed) formats.

CONCLUSION

A system and method has been shown in the above embodiments for the effective implementation of a method of rewarding the viewing of advertisements based on eye-gaze patterns. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by software/program, computing environment, or specific computing hardware.

The above enhancements are implemented in various computing environments. For example, the present invention may be implemented on a conventional IBM PC or equivalent, multi-nodal system (e.g., LAN) or networking system (e.g., Internet, WWW, wireless web). All programming and data related thereto are stored in computer memory, static or dynamic, and may be retrieved by the user in any of: conventional computer storage, display (i.e., CRT) and/or hardcopy (i.e., printed) formats. The programming of the present invention may be implemented by one of skill in the art of reading recognition, computer user interface programming, and web-based programming.

What is claimed is:

1. A method of paying users for viewing advertisements comprising:
   (a) determining, by a processor, viewer interaction with content of rendered advertisements based on eye-gaze patterns, said gaze patterns comprising any of the following: non-reading gaze, skimming gaze, or reading gaze, said determination of viewer interaction based on accumulated numerical evidence of eye movement in both X and Y directions, said numerical evidence independent of gaze time and factoring both incremental and decremental values;
   (b) recording, in a storage, viewer interests based on determination in (a) when said accumulated numerical evidence crosses a threshold;
   (c) computing payments based on viewer activity, and
   (d) disbursing payments based on said computed payments.

2. A method of paying users for viewing advertisements, as per claim 1, wherein said advertisements are distributed via any of the following networks: a local area network (LAN), a wide area network (WAN), the Internet, or a wireless network.

3. A method of paying users for viewing advertisements, as per claim 1, wherein said advertisements are displayed on an electronic display.

4. A method of paying users for viewing advertisements, as per claim 1, wherein said payments comprises monetary payments.

5. A method of paying users for viewing advertisements, as per claim 1, wherein said payments are computed in (c) based on any of the following: level of viewer interaction with said rendered advertisements, amount of content interacted with by the viewer, and the value of the text interacted with by the viewer.

6. A method of paying users for viewing advertisements, as per claim 5, wherein said level of viewer interaction comprises determining if said viewer is reading, skimming, or scanning said rendered content of said advertisement.

7. A method of paying users for viewing advertisements, as per claim 1, wherein said payments are computed based on both said viewer activity and previously recorded viewer interests.

8. A method of paying users for viewing advertisements, as per claim 7, wherein said previously recorded viewer interests are received over a network from a remote database.

9. A method of paying users for viewing advertisements, as per claim 8, wherein said recorded viewer interests are transferred to be stored in said remote database over said network.

10. A method of paying users for viewing advertisements, as per claim 9, wherein said network is any of the following: local area network (LAN), wide area network (WAN), wireless network, or the Internet.

11. A method of paying users for viewing advertisements, as per claim 1, wherein said payments are disbursed to any of the following: viewer, sponsor of the advertisement, creator of advertisement.

12. A method for rewarding viewers of Internet advertisements based on varying levels of interaction, said method comprising:
 (a) determining, by a processor, varying levels of viewer interaction with content of advertisements rendered over the Internet, said varying levels comprising at least: non-reading gaze, skimming gaze, or reading gaze, said determination of varying levels of viewer interaction based on an accumulated numerical evidence of eye movement in both the X and Y directions, said numerical evidence independent of gaze time and factoring both incremental and decremental values;
 (b) recording, in a storage, viewer interests based on determination in (a) when said accumulated numerical evidence crosses a threshold;
 (c) computing payments for viewing advertisements based on said determined level of viewer interaction, and
 (d) disbursing payments based on said computed payments in (c).

13. A method for rewarding viewers of Internet advertisements based on varying levels of interaction, as per claim 12, wherein said recorded viewer interests are transferred to be stored in a remote database over a network.

14. A method for rewarding viewers of Internet advertisements based on varying levels of interaction, as per claim 13, wherein, in addition to said determined level of viewer interaction, said payments are computed based on previously recorded viewer interests stored in said remote database.

15. A method for rewarding viewers of Internet advertisements based on varying levels of interaction, as per claim 12, wherein said payments are disbursed to any of the following: viewer, sponsor of the advertisement, creator of advertisement.

16. A method to reward users for viewing Internet advertisements rendered in a display comprising:
 (a) determining, by a processor, amount or proportion of content interacted with by a viewer, said content associated with rendered advertisements and said determination based on tracking eye-gaze patterns, said determination based on an accumulated numerical evidence of eye movement in both the X and Y directions, said numerical evidence independent of gaze time and factoring both incremental and decremental values;
 (b) recording, in a storage, viewer interests in said rendered content of said advertisements based on said determination in (a) when said accumulated numerical evidence crosses a threshold;
 (c) computing payments for viewing advertisements based on amount or proportion of content interacted with in (a), and
 (d) disbursing payments based on said computed payments in (c).

17. A method to reward users for viewing Internet advertisements rendered in a display, as per claim 16, wherein said recorded viewer interests are transferred to be stored in a remote database over a network.

18. A method to reward users for viewing Internet advertisements rendered in a display, as per claim 17, wherein, in addition to said amount or proportion of content interacted with, said payments are computed based on previously recorded viewer interests stored in said remote database.

19. A method to reward users for viewing Internet advertisements rendered in a display, as per claim 18, wherein said network is any of the following: local area network (LAN), wide area network (WAN), wireless network, or the Internet.

20. A method to reward users for viewing Internet advertisements rendered in a display, as per claim 16, wherein said payments are disbursed to any of the following: viewer, sponsor of the advertisement, creator of advertisement.

\* \* \* \* \*